Sept. 12, 1967 S. Y. MAEDA Plant Pat. 2,767
NECTARINE TREE
Filed Aug. 25, 1966
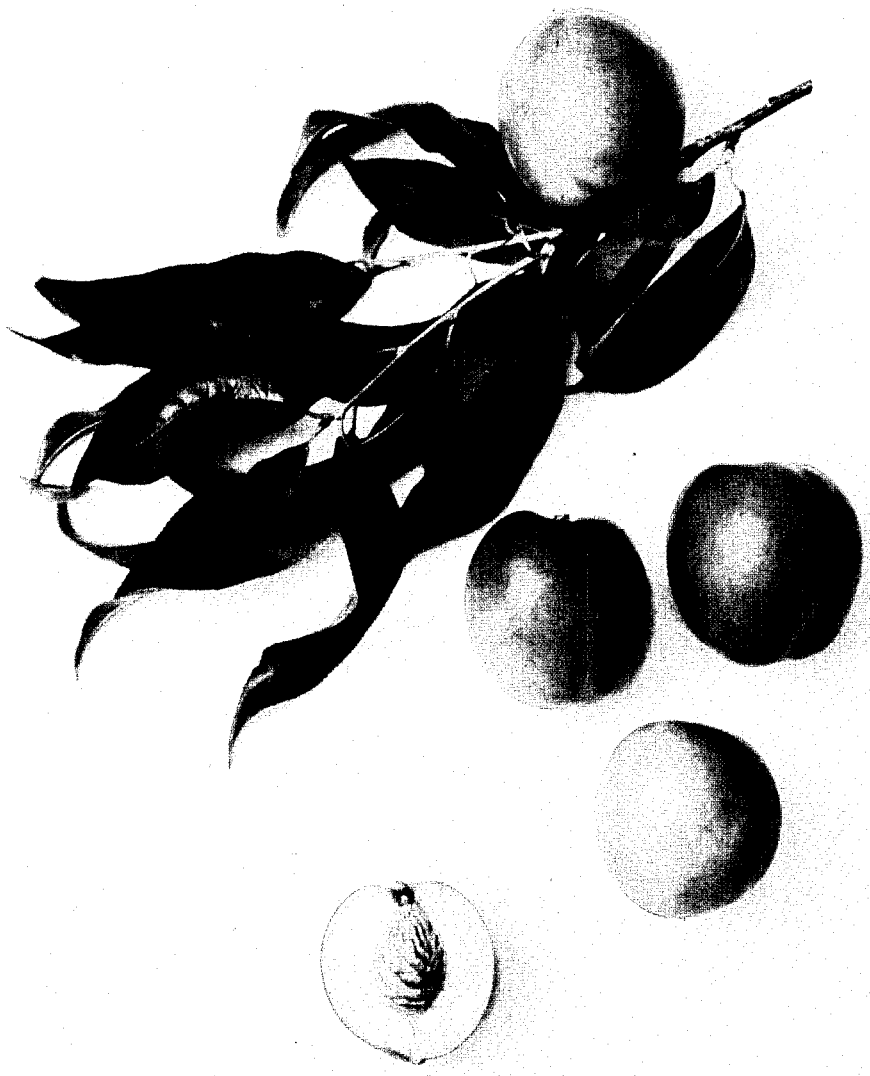
INVENTOR
Samuel Y. Maeda
BY
Webster & Webster
ATTORNEYS United States Patent Office Plant Pat. 2,767
Patented Sept. 12, 1967

2,767
NECTARINE TREE

Samuel Y. Maeda, Livingston, Calif., assignor to Kim Bros., Reedley, Calif., a co-partnership doing business with the fictitious name and style of Reedley Nursery Filed Aug. 25, 1966, Ser. No. 575,196
1 Claim. (Cl. Plt.—41)

This discovery relates to a new and distinct variety of nectarine tree which bears yellow flesh, freestone fruit having yellow skin overspread, in substantially its entirety, with red.

The present variety of nectarine tree is primarily characterized, as to novelty, by the relatively early bearing of commercially desirable fruit; the tree and its fruit—other than the earlier ripening of the latter—being generally the same as the Early Sun Grand (United States Plant Patent No. 1,420). Under the same or comparable growing conditions, the fruit of the present variety ripens and is in harvest approximately ten days earlier than the Early Sun Grand.

I discovered the present variety growing as a bud mutation on an Early Sun Grand nectarine tree in my orchard located near Livingston, Merced County, Calif. Subsequent to its discovery and recognition by me of its novel characteristic as above, the variety was asexually reproduced, on my behalf, by a commercial nursery located near Reedley, Fresno County, Calif.; such reproduction having been accomplished by budding. The budded trees were planted in my orchard located as aforesaid, and upon bearing, such reproductions were found to be true to the original bud mutation in all respects.

The drawing is an illustration, by photographic reproduction in color, of a twig with leaves, and an attached fruit; other whole fruit being shown detached, and half of another fruit cut to show the flesh, and with the stone remaining in place.

Referring now more specifically to the pomological details of this new and distinct variety of nectarine tree, the following is an outline description thereof; all major color plate identifications, by comparison with fresh specimens, being by reference to Maerz and Paul Dictionary of Color, except where common terms of color definition are employed.

Tree:
- *Size.*—Medium.
- *Vigor.*—Medium.
- *Growth.*—Spreading.
- *Form.*—Round topped.
- *Hardiness.*—Half hardy.
- *Production.*—Medium productive.
- *Bearing.*—Regular bearer.

Trunk:
- *Size.*—Medium.
- *Texture.*—Medium.

Branches:
- *Size.*—Medium.
- *Texture.*—Medium.
- *Color.*—Gray.
- *Lenticels.*—Number—numerous. Size—medium.

Leaves:
- *Size.*—Medium. Average length—5½". Average width—1½".
- *Form.*—Lanceolate; acutely pointed.
- *Thickness.*—Medium.
- *Texture.*—Smooth.
- *Margin.*—Crenate.
- *Petiole.*—Length—short. Thickness—medium.
- *Glands.*—Average number—four. Size—medium. Form—reniform. Position—on petiole and base of blade; opposite. Color—green.
- *Stipules.*—None.
- *Color.*—Top side—medium green (23–L–7). Under side—lighter green (22–J–5).

Flower buds:
- *Hardiness.*—Half hardy.
- *Size.*—Medium.
- *Length.*—Medium.
- *Form.*—Plump; free.

Flowers:
- *Blooming period.*—Date of first bloom—Mar. 6, 1966. Date of full bloom—Mar. 14, 1966. Medium, as compared with other varieties.
- *Size.*—Large.
- *Color.*—Pink.

Fruit:
- *Maturity when described.*—Hard ripe—June 8, 1966.
- *Date of first picking.*—June 2, 1966.
- *Date of last picking.*—June 12, 1966.
- *Size.*—Uniform; medium. Average diameter axially—2⅜". Average transversely in suture plane—2½".
- *Form.*—Unsymmetrical; globose to oblong.
- *Suture.*—Distinct; extends from base to beyond apex with marked depression beyond pistil point.
- *Ventral surface.*—Rounded slightly.
- *Lips.*—Unequal.
- *Cavity.*—Elongated in suture plane with suture showing on both sides. Average depth—½". Average breadth—⅝".
- *Base.*—Rounded.
- *Apex.*—Depressed.

Skin:
- *Thickness.*—Medium.
- *Texture.*—Medium.
- *Tenacity.*—Tenacious to flesh.
- *Tendency to crack.*—None.
- *Down.*—Wanting.
- *Color.*—Yellow (9–L–4), blushed with red (7–H–6) on sunny side, shading to lighter red (5–L–6)—speckled and mottled—on substantially the remainder.

Flesh:
- *Amygdalin.*—Wanting.
- *Juice.*—Moderate.
- *Texture.*—Firm; crisp.
- *Fibers.*—Few.
- *Ripens.*—Evenly.
- *Flavor.*—Acid to subacid.
- *Aroma.*—Wanting.
- *Eating quality.*—Fair to good.
- *Color.*—Yellow (10–L–5).

Stone:
- *Type.*—Free.
- *Size.*—Small. Average length—1½". Average breadth—1". Average thickness—¾".
- *Form.*—Oblong; obovoid.
- *Base.*—Straight.
- *Hilum.*—Narrow.
- *Apex.*—Acute.
- *Sides.*—Equal.
- *Surface.*—Regularly furrowed.
- *Ridges.*—Rounded; continuous.
- *Ventral edge.*—Thick.
- *Dorsal edge.*—Full, with shallow groove.
- *Color.*—Light or yellowish tan (13–L–8).

Use: Market.
Keeping quality: Medium to good.
Shipping quality: Medium to good.

The tree and its fruit herein described may vary in slight detail due to climatic and soil conditions under which the variety may be grown; the present description being of the variety as grown in the Central Valley of California.

The following is claimed:

A new and distinct variety of nectarine tree, substantially as illustrated and described, which is a regular bearer of yellow flesh freestone fruit having yellow skin overspread with red; the variety, while generally similar to the Early Sun Grand, being characterized, as to novelty, by fruit which ripens approximately ten days earlier.

No references cited.

ABRAHAM G. STONE, *Primary Examiner.*

ROBERT E. BAGWILL, *Examiner.*